US006489785B2

(12) United States Patent
McAllister

(10) Patent No.: US 6,489,785 B2
(45) Date of Patent: Dec. 3, 2002

(54) COMPARATIVE CONTACTLESS CONDUCTIVITY DETECTOR

(75) Inventor: William H. McAllister, Saratoga, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 21 days.

(21) Appl. No.: 09/730,645

(22) Filed: Dec. 5, 2000

(65) Prior Publication Data

US 2002/0067174 A1 Jun. 6, 2002

(51) Int. Cl.[7] ................. G01R 27/08; G01R 27/26; G01N 27/00
(52) U.S. Cl. ............... 324/695; 324/693; 324/705; 324/71.1; 324/667
(58) Field of Search ................. 324/690, 693, 324/667, 453, 691, 679, 705, 71.1, 695

(56) References Cited

U.S. PATENT DOCUMENTS

| 4,374,644 A | * | 2/1983 | Armstrong | 436/63 |
| 5,210,500 A | * | 5/1993 | Pingel et al. | 324/667 |
| 5,528,133 A | * | 6/1996 | Saklikar | 324/71.1 |
| 5,572,115 A | * | 11/1996 | Strong et al. | 324/71.1 |
| 6,180,536 B1 | * | 1/2001 | Chong et al. | 438/745 |
| 6,203,683 B1 | * | 3/2001 | Austin et al. | 204/547 |

OTHER PUBLICATIONS

Jose A. Fracassi da Silva & Claudimir L. do Lago "An Oscillometric Detector for Capillary Electrophoresis", *Analytical Chemistry*, vol. 70, 1998, pp. 4339–4343.

Jiri Vacik, Jiri Zuska & Iva Muselasova, "Improvement of the Peformance of a High–Frequency Conductivity Detector for Isotachophoresis" Journal of Chromatography, 17,322, 1985, 5 pages.

Andress J. Zemann, Erhard Schnell, Dietmar Volger, & Glnther K. Bonn, "Contactless Conductivity Detection for Capillary Electrophoresis" Analytical Chemistry, vl. 70, 1998, pp. 563.567.

B. Gas, M. Demjanenko, and J. Vacik, "High–Frequency Contactless Conductivity Detection in Isotachophoresis", *Journal of chromatography*, 192(1980), pp. 253–257.

* cited by examiner

*Primary Examiner*—N. Le
*Assistant Examiner*—Anjan K. Deb

(57) ABSTRACT

A comparative conductivity detection system includes a sample channel assembly and a reference channel assembly. The sample channel assembly includes a sample-fluid channel, a drive electrode, and a detection electrode. The reference channel assembly includes a reference fluid channel, a drive electrode, and a detection electrode. The channels are formed as trenches in a planar substrate. Each electrode is capacitively coupled to its respective channel through a planar cover over the substrate. The drive electrodes are driven anti-synchronously (180° out of phase), while the signals induced in the detection electrodes are summed. The summed detection signal indicates the comparative conductivity of the sample and reference fluids. The reference fluid can, for example, include non-sample components of the sample fluid so that artifacts due to the non-sample components are cancelled in the comparative conductivity detector output. Other applications use a reference fluid that is suspected to be a complete or partial match for the sample fluid. In that case, a high degree of cancellation can aid in identification of the sample components. The comparative contactless conductivity detector can be used with a wide variety of chemical separation techniques, including capillary zone electrophoresis and isotachophoresis.

10 Claims, 3 Drawing Sheets

COMPARATIVE CONTACTLESS CONDUCTIVITY DETECTOR

BACKGROUND OF THE INVENTION

The present invention relates to analytical chemistry and, more particularly, to conductivity detectors used, for example, to detect sample fluid components as they flow in a channel through a detection region. A major objective of the invention is to provide for comparative contactless conductivity detection.

Much of modern progress in the medical, pharmaceutical, environmental, industrial-process, forensic, and other sciences can be attributed to advances in analytical chemistry. One important class of analytical tools separates components of a sample fluid (typically, a mixture of sample components and non-sample components such as carriers, buffers, and surfactants) by moving them at different rates along a separation channel. Once the components are separated, it is usually desirable to quantify, and, perhaps, identify the components. This typically requires detection of the components. Detectors are available to monitor certain parameters, such as conductivity, fluorescence, or absorption of ultraviolet (UV) electromagnetic energy as the components pass through a detection region.

Conductivity detection is appealing for electrophoresis, in which components are separated by an electric field according to their electrophoretic mobilities. Components separated by electrophoresis necessarily have a measurable electrical conductivity associated with their electrophoretic mobilities. More generally, conductivity detection is useful for detecting the components with measurable conductivity regardless of how they arrive at the detector region.

Conductivity detection can be implemented by locating electrodes on the interior walls of an electrophoretic channel, in direct contact with the sample fluid. Typically, drive and detection electrodes oppose each other across a transverse width or diameter of the electrophoretic channel. However, since the electrodes are in contact with the sample fluid, electrochemical reactions at the electrodes can affect both the electrodes and the sample. Such interaction can cause undesirable artifacts within a run and can undermine repeatability between runs. This undesirable interaction between sample and electrodes is avoided by "contactless" conductivity detection.

In contactless conductivity detection, electrodes are capacitively coupled to the sample fluid through a channel wall. To this end, the electrodes can be formed on the exterior surface of the channel wall. Since the electrodes are not in contact with sample fluid, artifacts due to chemical interactions at the electrodes are eliminated and reproducibility is improved.

Contactless conductivity detection is taught by Jose A. Fracassi da Silva & Claudimir L. do Lago "An Oscillometric Detector for Capillary Electrophoresis", *Analytical Chemistry*, vol. 70, 1998, pp. 4339–4343; Jirí Vacik, Jirí Zuska & Iva Muselasova, "Improvement of the Performance of a High-Frequency Conductivity Detector for Isotachophoresis" Journal of Chromatography, 17,322, 1985, 5 pages; Andress J. Zemann, Erhard Schnell, Dietmar Volger, & Günther K. Bonn, "Contactless Conductivity Detection for Capillary Electrophoresis" Analytical Chemistry, V.70, 1998, pp. 563–567. In addition, an anti-synchronously driven contactless conductivity detector is the subject of commonly owned U.S. patent application Ser. No. 09/576,690 filed May 23, 2000, entitled "Sample-analysis system with anti-synchronously driven contactless conductivity detection" by Gary B. Gordon and Tom A. vande Goor.

All of the foregoing contactless conductivity detectors are designed to characterize the conductivity profile over time of a fluid as it flows through a detection region of a fluid channel. However, it is often desirable to compare the conductivity profiles of two fluids. Generally, the profile of a sample fluid can be compared with the profile of a reference fluid to remove "uninteresting" profile features due to the carrier, buffer, surfactant, etc. In industrial-process applications, it is often important to determine whether or not the composition of a process fluid has changed. In forensic applications, it is often desirable to determine whether or not two samples have the same composition.

Comparative conductivity profiles can be obtained by subtracting two independently obtained "absolute" fluid conductivity profiles. However, high-level background signals corresponding to non-sample components can make it difficult to obtain precise conductivity profiles. Furthermore, errors in the absolute profiles are exacerbated when they are subtracted to obtain the desired comparison. What is needed is a system that can provide more error-free comparative conductivity profiles.

SUMMARY OF THE INVENTION

The present invention provides a comparative contactless-conductivity detection system with at least two channel assemblies, each with a fluid channel, drive electrodes, and detection electrodes. The drive electrodes are driven so that detection signals are induced at the detection electrodes; these detection signals are combined to provide a detector signal corresponding to a difference in conductivities between the two fluids. Preferably, drive electrodes are driven anti-synchronously and the detection electrodes are electrically connected so that the detection signals sum at a common node. In view of the anti-synchronous drive, the sum corresponds to the difference between the conductivities of the fluids. In other words, the detector signal represents the comparative conductivity of one the fluids relative to the other.

In a typical application, a first channel carries a sample fluid to be characterized, while a second channel carries a reference fluid with a known conductivity. The reference fluid conductivity can be constant or can vary in a known manner over time. For example, the reference fluid can be the same chemical as the buffer used in the sample fluid. The comparative signal would represent the sample components without the background associated with the buffer. In an isotachophoresis application, the reference fluid can have its conductivity vary spatially in a manner that generally mimics the sample fluid to reduce the background against which the signal of interest is to be read.

Alternatively, the reference fluid can be another sample of known or unknown composition. The comparative conductivity detector provides a clear indication when two samples have the same composition. In addition, the comparative conductivity detector would help pinpoint small differences in composition. Known reference fluids can be used to confirm a match between a sample and reference chemical. Reference fluids of unknown composition can be used in industrial-process and forensic applications where the similarity or identity of samples is the issue rather than the composition of the samples.

The invention applies to sample fluids whether or not the sample component fluids have been separated by some separation technique. For applications in which the sample-fluid components have been separated, the reference-fluid components may or may not be subject to the same separation forces as the sample-fluid components. If the reference fluid is intended to vary over time in a controlled fashion, the reference fluid is in general not subjected to separation forces. On the other hand, the reference fluid should be subjected to the same separation forces as the sample fluid if component-by-component comparison is to be achieved.

The present invention provides for fabricating the sample and reference channels in a monolithic substrate using, for example, integrated-circuit manufacturing techniques. The resulting micro-fluidic platform provides a remarkably convenient way to create a reference channel that is precisely matched to the sample channel. In addition, the channels can be in close proximity, thereby minimizing artifacts due to differences in ambient conditions at the channels. For example, the temperatures of the sample and reference fluids can be made substantially identical, thereby removing temperature as a noise source in the measurement. Including the reference channel within the micro-fluidic platform also enhances the ease with which one can change and control the reference fluid.

In summary, comparative conductivity detection provides a stronger signal of interest by reducing the influence of high background signal levels. When implemented using precision monolithic manufacturing techniques, the invention can minimize artifacts due to environmental changes. Furthermore, the invention provides considerable flexibility in selecting reference fluids to match the intended application. These and other features and advantages are apparent from the description below with reference to the following drawings.

DETAILED DESCRIPTION OF THE PREFERRED EMBODIMENTS

Figure 1:
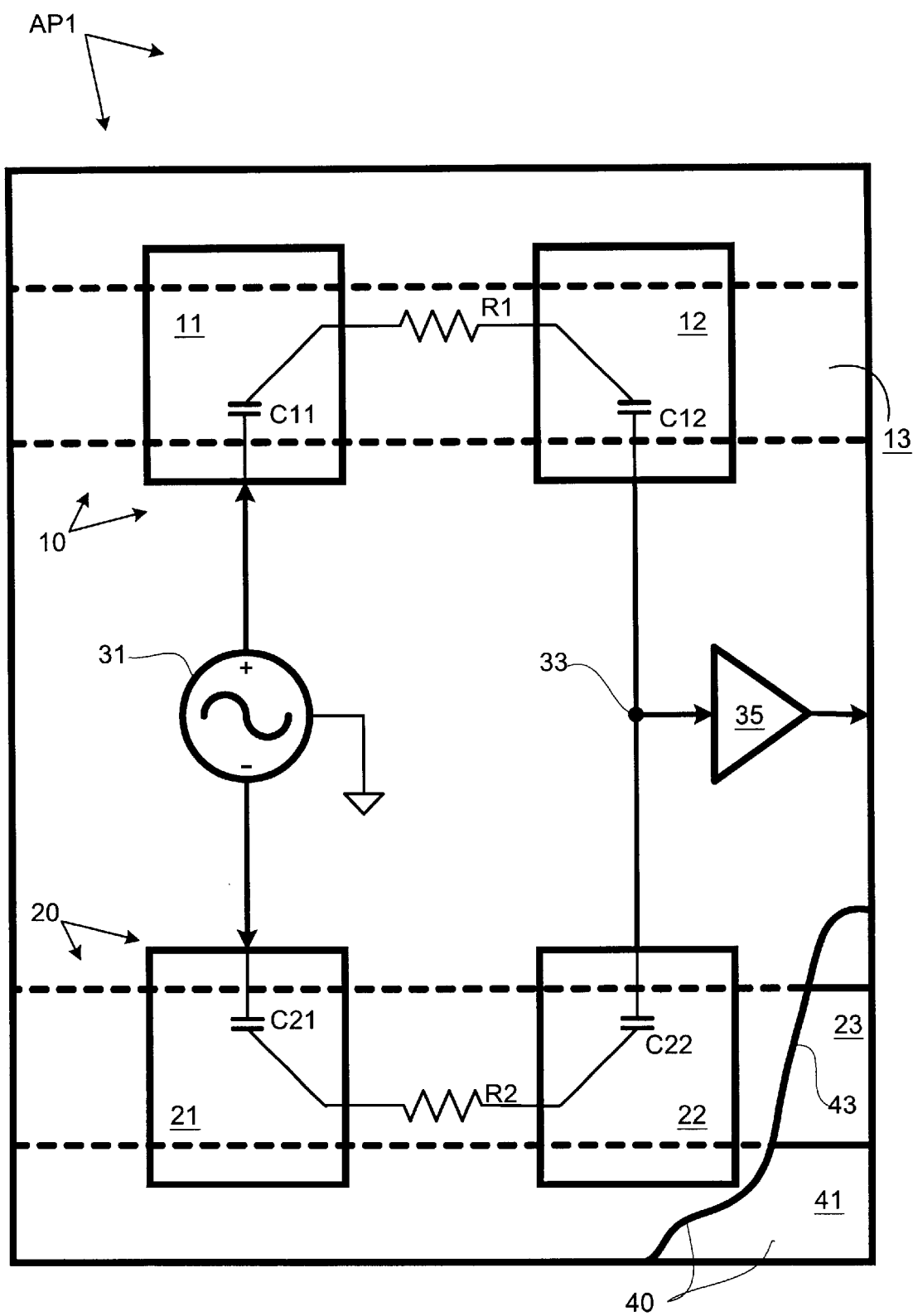
FIG. 1 is a schematic plan view of a comparative conductivity detection system in accordance with the present invention.

In accordance with the present invention, a comparative contactless conductivity detection system AP1 comprises nominally identical first and second channel assemblies 10 and 20, an oscillator 31, a summing node 33, and a detector 35, as shown in FIG. 1. Planar assembly 40 includes a substrate 41 and a cover 43. First channel assembly 10 includes a first drive electrode 11, a first detection electrode 12, and a first channel 13 formed as a trench in substrate 41. Second channel assembly 20 includes a second drive electrode 21, and a second detection electrode 22, and a second channel 23 formed as a trench in substrate 41. Electrodes 11, 12, 21, and 22 are plated onto cover 43, which forms a top wall for channels 13 and 23.

Figure 2:
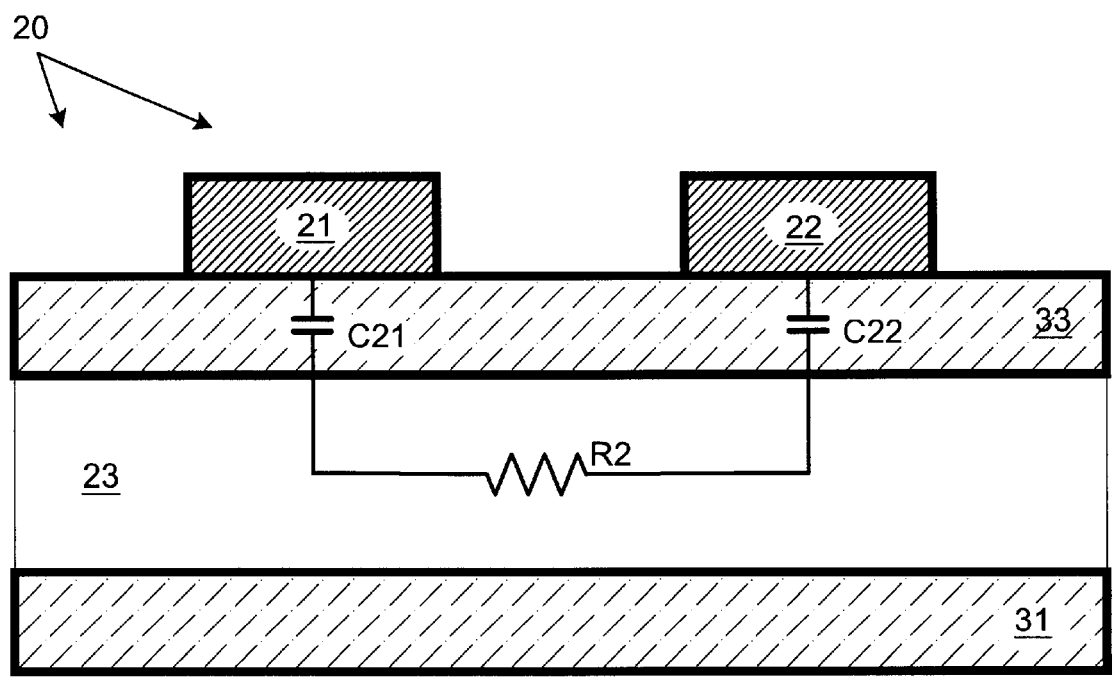
FIG. 2 is a schematic side view of the system of FIG. 1.

Each electrode 11, 12, 21, 22 is capacitively coupled to fluid in the adjacent channel 13, 23, through cover 43; the electrode-fluid capacitance for each electrode 11, 12, 21, 22 is C11, C12, C21, and C22, respectively. The fluid between first channel electrodes 11 and 12 has an associated conductance, which is indicated in FIG. 1 by its reciprocal, resistance R1. Likewise, the fluid between second channel electrodes 21 and 22 has an associated conductance, which is indicated in FIG. 1 by resistance R2. The electrical path for channel assembly 20 is shown from another viewpoint in FIG. 2. The electrical path for channel assembly 10 is nominally identical to the electrical path for channel assembly 20.

Oscillator 31 drives electrodes 11 and 21 anti-synchronously, i.e., 180° out of phase, as indicated in FIG. 1. The oscillation frequency can be 500 kilohertz, but frequencies within an order of magnitude of that can be used to useful effect. The waveform transmitted to first drive electrode 11 results in a first detection signal at first detection electrode 12. The waveform transmitted to second drive electrode 21 results in a second detection signal at second detection electrode 22. If identical fluids fill channels 13 and 23, the anti-synchronous detection signals cancel at summing node 33, so that the comparative conductivity output signal from detector 35 is zero. Any differences in the fluids will result in imperfect cancellation and thus a non-zero signal from detector 35.

Figure 3:
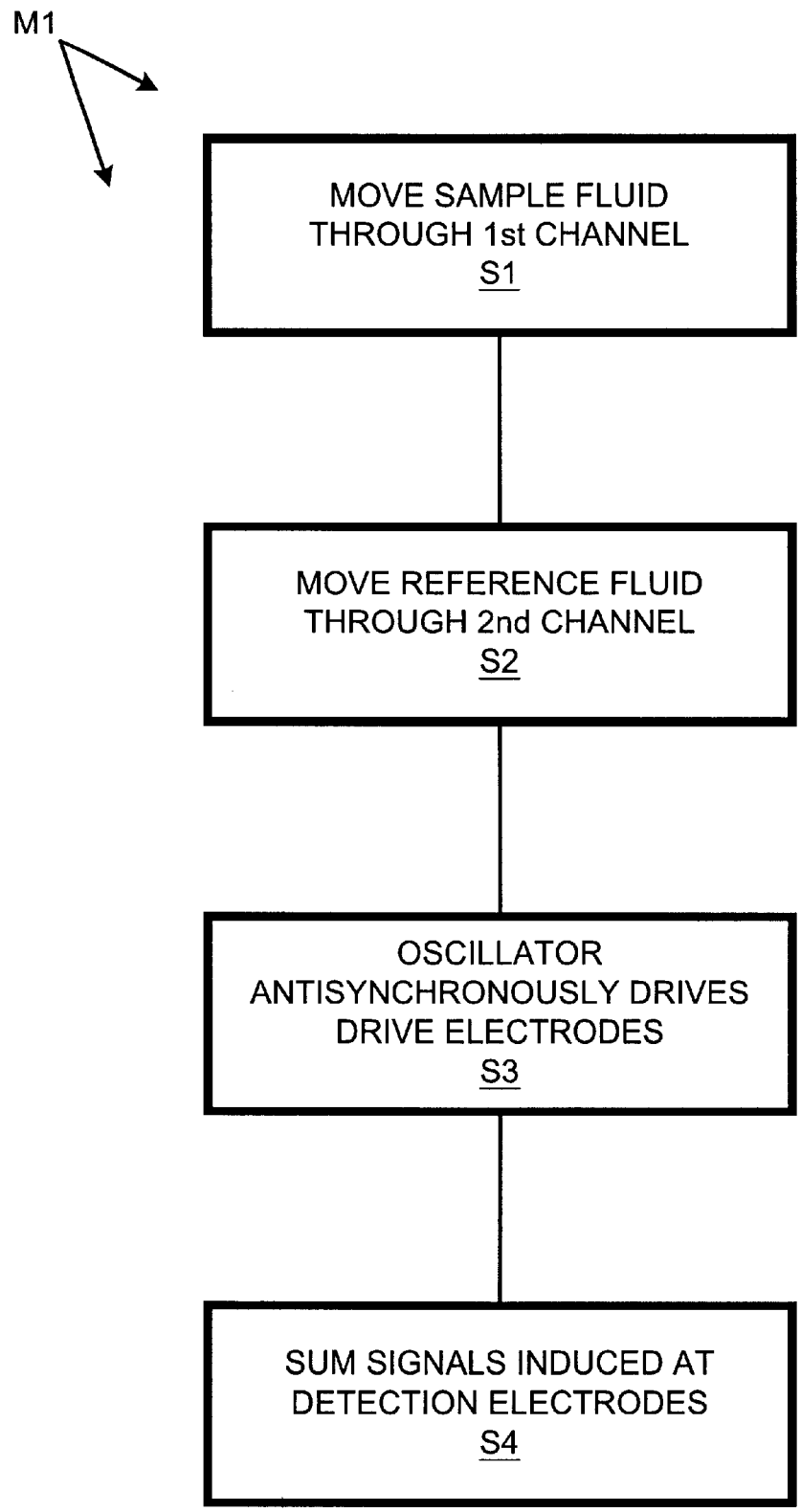
FIG. 3 is a flow chart of a method of the invention practiced in the context of the system of FIG. 1.

A method M1 of the invention practiced in the context of the conductivity detector AP1 is flow-charted in FIG. 3. Method M1 comprises four steps. Step S1 involves moving a first fluid through a first channel. Step S2 involves moving a second fluid through a second channel. Step S3 involves driving electrodes capacitively coupled to each channel. Step S4 involves detecting the sum of the signals induced in the detection electrodes associated with the respective channels.

In general, all four steps are performed concurrently. However, in some cases, one or both fluids can be stationary during detection. For example, step S2 can involve pre-filling the second channel with reference fluid, and then performing steps S1, S3, and S4. The reference fluid can be a fluid that matches a carrier fluid or a buffer mixed with sample components in the sample fluid in the first channel. The main advantage of such a realization of the invention is that the signal background attributable to the buffer or carrier is minimized.

In the case of isotachophoresis (ITP), conductivity tends to vary as a step-function of time. In the case of ITP, the reference fluid could be the leading buffer. For greater background suppression, a reference fluid with similarly monotonically varying conductivity, but without the steps can be used for enhanced background conductivity cancellation. This can be achieved by supplying a time-varying gradient mixture of leading and trailing buffers. In this case, the reference fluid is not subjected to the constant longitudinal electric field used to separate components of the sample fluid.

Effective artifact removal can be achieved by using a reference fluid that includes as many as possible of the non-sample components of the sample fluid. For example, the first channel can include a sample mixed with a carrier, reagents left over from previous sample treatments, and surfactants or other additives. The second channel can be filled with a fluid including the carrier, reagents, and additives, but not the sample. In the context of a separation system, the same separation treatment could be applied to both channels. The sample and reference channels would be subjected to the same separation forces. Detection peaks associated with non-sample components would be cancelled so that detection peaks associated with sample components would be more salient.

For some applications, the reference fluid can be selected because it is suspected as a complete or partial match for the sample. If a sample mixture matches the composition of a proposed matching mixture, a null detection will result. Deviations from full cancellation can flag components present in one but not the other of the two mixtures.

In industrial-process applications, degree of similarity may be more important than composition. Conductivity detection is effective for use in monitoring salient differences in product composition and quality. For example, in a beverage-manufacturing application, quality control can involve comparing product samples with an exemplary reference beverage to ensure "flavor matching".

In forensic applications, the presence of a match, e.g., between a material associated with a defendant and a material found at the crime scene, may be more important that determining the composition of a sample. In such an application, if comparative conductivity detection is used to determine a match, the composition of the reference fluid need not be known.

If conductivity detection is to be applied as components are being separated, the separation technique applied to the sample fluid can also be applied to the reference fluid. However, this is not necessary, where the reference fluid has an unvarying conductivity. In that case, the reference fluid can be motionless within the channel or simply flow through the channel without separation activity.

In the illustrated embodiment, drive and detection electrodes are spaced longitudinally along planar fluid channels. In an alternative planar configuration, drive and detection electrodes are arranged across the channels. This approach permits a small detection volume for greater spatial resolution at the cost of reduced sensitivity. Furthermore the invention provides for longitudinal and transverse electrode arrangements with capillary instead of planar channels.

The present invention is not limited to systems with a single reference channel; plural reference channels are provided for. For example, in an isotachophoresis system, a leading buffer reference channel and a trailing buffer reference channel can be used. A switch can be used to select the active reference channel so that the conductivity of a detected component can be compared with either buffer.

The present invention has industrial applicability in the medical, pharmaceutical, environmental, industrial process, and forensic fields. In the latter two cases, the invention provides for sample matching using reference fluids of unknown composition. Many applications require a reference fluid with a known composition. For sample identification purposes, the reference fluid can be subjected to the same separation forces as the sample fluid. If the objective is simply to reduce background signal, the reference need not be subjected to these forces. These and other variations upon and modifications to the present invention are provided for by the present invention, the scope of which is defined by the following claims.

What is claimed is:

1. A comparative contactless conductivity detector system comprising:

first and second flow channels having respective channel walls, drive electrodes, and detection electrodes, said detection electrodes being respectively coupled to said drive electrodes resistively and capacitively through respective channel walls and through respective channels;

detection electronics connected to said detection electrodes for detecting a difference in the magnitudes of detection signals induced in said detection electrodes; and an oscillator coupled to said drive electrodes so that they induce said detection signals.

2. A system as recited in claim 1 further comprising a monolithic substrate in which said first and second flow channels are defined.

3. A system as recited in claim 1 wherein said drive electrodes are driven anti-synchronously and said detection electrodes are electrically connected to each other.

4. A system as recited in claim 1 wherein said second channel includes a reference fluid with a reference conductivity that is known prior to detection.

5. A system as recited in claim 4 wherein said reference conductivity varies as a function of time, said function being known before detection.

6. A method of detecting the conductivity of a fluid over time comprising the concurrent steps of:

causing a first fluid to flow in a first channel past a first drive electrode and a first detection electrode;

causing a second fluid to flow in a second channel past a second drive electrode and a second detection electrode;

driving said first and second drive electrodes so as to induce detection signals at said first and said second detection electrodes; and detecting a difference in the magnitudes of said detection signals.

7. A method as recited in claim 6 wherein said driving involves driving said drive electrodes are anti-synchronously and said detecting involves detecting a sum signal at a node connected to both said first and said second detection electrodes.

8. A method as recited in claim 6 wherein said second fluid has a known reference conductivity.

9. A method as recited in claim 6 wherein said reference conductivity varies as a known function of time.

10. A method as recited in claim 9 wherein said function is monotonic.

* * * * *